US00PP31092P3

(12) United States Plant Patent
Stemkens

(10) Patent No.: US PP31,092 P3
(45) Date of Patent: Nov. 19, 2019

(54) ***PHLOX* PLANT NAMED 'PHMZ0002'**

(50) Latin Name: *Phlox paniculata*
Varietal Denomination: PHMZ0002

(71) Applicant: Ditoplant Export BV, Noordwijkerhout (NL)

(72) Inventor: Henricus Godefridus Wilhelmus Stemkens, Andijk (NL)

(73) Assignee: DITOPLANT EXPORT BV, Noordwijkerhout (NL)

( * ) Notice: Subject to any disclaimer, the term of this patent is extended or adjusted under 35 U.S.C. 154(b) by 0 days.

(21) Appl. No.: 15/932,955

(22) Filed: May 30, 2018

(65) Prior Publication Data

US 2018/0359895 P1 Dec. 13, 2018

(30) Foreign Application Priority Data

Jun. 9, 2017 (EP) ..... PBR 2017/1506

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
See application file for complete search history.

*Primary Examiner* — Susan McCormick Ewoldt
(74) *Attorney, Agent, or Firm* — Penny J. Aguirre

(57) ABSTRACT

A new and distinct cultivar of *Phlox* plant named 'PHMZ0002,' characterized by its large sized inflorescences, having a lilac color with a white eye, deep green leaves, and a compact, upright, and branched plant habit.

1 Drawing Sheet

Latin name of the genus and species of the plant claimed: *Phlox paniculata.*

Varietal denomination: 'PHMZ0002'.

CROSS-REFERENCE TO RELATED APPLICATIONS

This application claims priority to European Community Plant Variety Office (CPVO) Plant Breeder's Rights Application No. 2017/1506 filed on Jun. 9, 2017, the entire contents of which is incorporated by reference herein.

BACKGROUND

The claimed plant is a new and distinct cultivar of the *Phlox* plant, botanically known as *Phlox paniculata*, and hereinafter referred to by the name 'PHMZ0002' or "the new *Phlox*." Clones or propagules of the claimed plant are identical to the original plant in all distinguishing characteristics.

The parents of 'PHMZ0002' are unknown. The new *Phlox* is a product of a planned breeding program in an open pollination cultivated area in Enkhuizen, The Netherlands in August 2009.

'PHMZ0002' was also selected in Enkhuizen, Netherlands as one flowering plant in July 2010 and immediately reproduced. Thus, asexual reproduction of 'PHMZ0002' was accomplished when vegetative cuttings were propagated in July 2010 in a greenhouse in Enkhuizen, The Netherlands.

The new *Phlox* has large sized inflorescences having a lilac color with a white eye, deep green leaves, and an upright plant habit.

The new *Phlox* is also known under the tradename "Sweet Summer Lilac Wink".

SUMMARY

Horticultural examination of plants grown from cuttings of the plant initiated in the fall of 2010, and continuing thereafter, has demonstrated that the combination of characteristics as disclosed herein for 'PHMZ0002' are firmly fixed and are retained through successive generations of asexual reproduction.

The claimed plant has not been observed under all possible environmental conditions. The phenotype may vary somewhat with variations in environment and cultural practices such as temperature, light intensity, and day length, without, however, any variance in genotype.

The following traits disclosed herein have been repeatedly observed and are determined to be unique characteristics of 'PHMZ0002'. At least these characteristics, in combination, distinguish 'PHMZ0002' as a new and distinct cultivar of *Phlox:*

1. Plants of the new *Phlox* have improved branching relative to other plants of the botanical class.
2. Plants of the new *Phlox* have darker green leaves relative to other plants of the botanical class.
3. Plants of the new *Phlox* are shorter relative to other plants of the botanical class.

BRIEF DESCRIPTION OF THE PHOTOGRAPHS

The accompanying colored photograph illustrates the overall appearance of the new *Phlox*, showing the colors as true as it is reasonably possible to obtain in colored reproductions of this type. Colors in the photograph may differ slightly from the color values cited in the detailed botanical description, which accurately describe the colors of the new *Phlox*. The photograph was taken in July 2016 in Andijk, The Netherlands, where the plant was about 14 weeks old and was grown in a 13 cm pot.

FIG. 1 shows a close-up view of typical flowers of 'PHMZ0002.'

DETAILED BOTANICAL DESCRIPTION

The aforementioned photograph describes a plant grown in Enkhuizen, The Netherlands, under commercial testing practice during the summer in containers in an outdoor nursery. During the production of the plant, day temperatures ranged from 12° Celsius to 30° Celsius, and night temperatures ranged from 2° Celsius to 16° Celsius. The plant was propagated by cuttings and was growing in a container for four months when the photograph was taken. In the following description, descriptions of color are made with reference to The Royal Horticultural Society Colour Chart, 2001 Edition, except where general terms of ordinary dictionary significance are used.

Table 1 below shows a comparison between the new *Phlox* and a similar variety, 'DITOMSUR' (U.S. Plant Pat. No. 21,109).

TABLE 1

| | 'PRMZ0002' | 'DITOMSUR' |
|---|---|---|
| Flower color | Lilac with white eye | Violet with white eye |
| Branching | More | Less |
| Leaf color | Deep green | Medium green |

Botanical classification: *Phlox paniculata* 'PHMZ0002'.

Parentage:

*Female, or seed, parent.*—Unnamed selection of *Phlox paniculata*, not patented.

*Male, or pollen, parent.*—Unnamed selection of *Phlox paniculata,* not patented.

Propagation:

*Type.*—By cuttings.

*Time to initiate roots.*—About 2 weeks at 15° Celsius to 25° Celsius.

*Time to produce a rooted young plant.*—About 5 weeks at 15° Celsius to 25° Celsius.

*Root description.*—Fibrous and thin, having a color close to N155D.

*Rooting habit.*—Moderate branching that is fairly dense.

Plant description:

*Plant form/habit.*—Compact and upright habit, with a moderately vigorous growth habit.

*Branching habit.*—Freely branching habit with about eight lateral branches per plant; pinching enhances branching.

*Plant height.*—About 38.2 cm in a pot, and 55 cm in a garden.

*Plant width.*—About 35.2 cm.

*Lateral branches.*—Length depends on growing conditions, but generally about 24.2 cm; diameter is about 5 mm. The internode length is about 2.7 cm. The branches are fairly strong. The texture of the branches is smooth and glabrous. The color is close to 147D.

Foliage description:

*Arrangement.*—Opposite, simple.

*Length.*—About 12.3 cm.

*Width.*—About 4.2 cm.

*Shape.*—Narrowly ovate.

*Apex.*—Acute.

*Base.*—Obtuse.

*Margin.*—Entire.

*Texture, upper and lower surfaces.*—Smooth and glabrous.

*Venation pattern.*—Pinnate.

*Color.*—Deep green, generally. The upper surface of developing leaves is darker than 147C and heavily flushed with N185A. The lower surface of developing leaves is darker than 147C. Fully expanded leaves have an upper surface close to 137B; venation close to 145C. Fully expanded leaves have a lower surface close to 137D; venation close to 145A.

*Petioles.*—Length is about 2.7 mm; diameter is about 3.2 mm. The texture of the upper and lower surface is smooth and glabrous. The color of the upper and lower surfaces is close to 145B.

Stem:

*Branching characteristics.*—From the bottom; new branches are made in the Spring.

*Quantity of main branches per plant.*—About 8 to 10.

*Color of stem.*—Close to 143A.

*Stem length.*—About 32.0 to 34.0 cm.

*Stem width.*—About 0.3 cm.

*Length of internodes.*—About 2 to 3.3 cm.

*Texture.*—Hirsute.

*Peduncle.*—Length of about 8.5 cm; diameter of about 4 mm; strength: strong; texture is smooth and glabrous; color is close to 146C.

Flower description:

*Flower type/habit.*—Single rotate flowers arranged in terminal compound panicles; flowers face mostly upright or are outwardly facing. Panicles are rounded and hemispherical in shape. The claimed plant has a freely flowering habit with about 60 flowers developing per inflorescence. In general, the blossoms/flowers include a large head with a plurality of light lilac flowers.

*Fragrance.*—Medium fragrance; sweet and pleasant.

*Natural flowering season.*—Flowering from July to September in The Netherlands.

*Postproduction longevity.*—Flowers last about eleven days on the plant.

*Flower buds.*—The height is about 1.2 cm. The diameter is about 3 mm. The shape is narrowly oblanceolate. The color is close to 70C; the lower half is close to N186A; the base is close to 145C to 145D.

*Inflorescence height.*—About 14 cm.

*Inflorescence diameter.*—About 9.8 cm.

*Flower diameter.*—About 3.5 cm.

*Flower depth.*—About 2.9 cm.

*Petals.*—Quantity per flower: typically five in a single whorl; petals fused at the base into a narrow tube. Length from throat: about 1.7 cm. Length fused: about 1.8 cm. Lobe width: about 1.3 cm. Lobe shape: roughly spatulate. Apex: rounded. Margin: entire. Texture, upper and lower surfaces: smooth, glabrous. Color of developing petals, upper surface: close to N87C; spots between about 86D and N155A; towards the throat about N87C to N87D; at the throat about N87B. Color of developing petals, lower surface: about 92A; tube is close to 92B. Color of fully expanded petals, upper surface: about N87D; spots between about 85D and N155A; towards the throat about darker than N88D; throat is close to N88D. Color of fully expanded petals, lower surface: close to N88D; tube, close to 85D.

*Sepals.*—Quantity per flower: typically five in a single whorl, fused towards the base. Length: about 8 mm. Width: about 1.6 mm. Shape: lanceolate. Apex: narrowly apiculate. Margin: entire. Texture, upper and lower surfaces: smooth, glabrous. Color of developing sepals, upper and lower surfaces: about N187C; towards the base is about 145D. Color of expanded sepals, upper and lower surfaces: about N187C; towards the margins is about 145C.

*Pedicels.*—Length: about 5 mm. Diameter: about 1 mm. Strength: strong. Texture: smooth, glabrous. Color: close to 144D.

*Reproductive organs.*—Androecium — Stamens: anthers and filaments fused to upper half of corolla tube; four anthers with two pollen sacs per anther. Color of filaments: close to 151D. Filament length: about 0.2 cm. Anther color: close to 151C. Anther length: about 0.1 cm. Pollen amount: none observed. Gynoecium — Pistil quantity per flower: one. Pistil length: about 1.6 cm. Stigma color: close to 144A. Style length: about 1.6 cm. Style color: close to N144B. Ovary color: close to 144B. Ovary length: about 0.2 cm. Ovary width: about 0.1 cm.

*Seed/fruit.*—Seed and fruit development have not been observed.

*Winter dormancy.*—In winter dormancy, the plant is not visual.

*Disease/pest resistance.*—Plants of the new *Phlox* have been observed to be tolerant to Downy Mildew. Plants of the new *Phlox* have not been observed to be resistant to pests or other pathogens common to *Phlox*.

*Garden performance.*—Plants of the new *Phlox* have been observed to have good garden performance and be tolerate to rain, wind, and temperatures ranging from —20° Celsius to 40° Celsius.

What is claimed is:

1. A new and distinct *Phlox* plant named 'PHMZ0002' as illustrated and described herein.

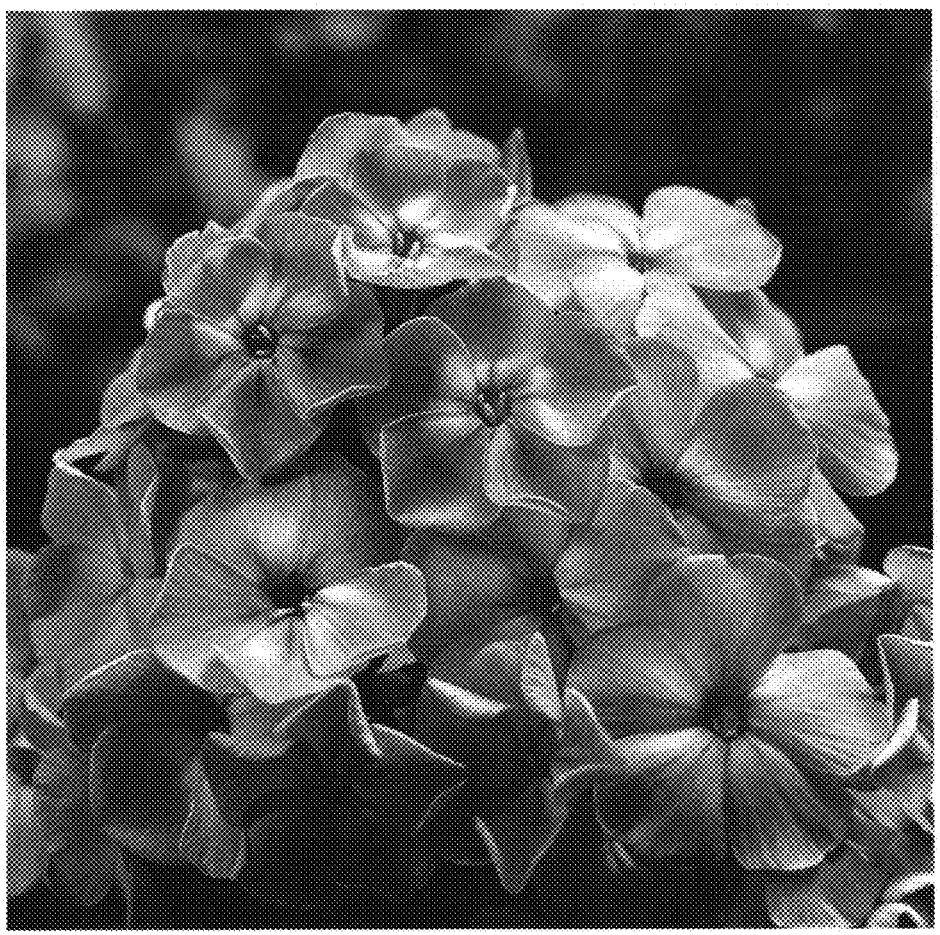

* * * * *